(12) United States Patent
Gaalswyk

(10) Patent No.: US 8,097,451 B2
(45) Date of Patent: Jan. 17, 2012

(54) SELF-CONTAINED DEPLOYABLE AUTOMATIC FACTORY BUILT ETHANOL PRODUCTION PLANT

(76) Inventor: Mark K Gaalswyk, Sherburn, MN (US)

( * ) Notice: Subject to any disclaimer, the term of this patent is extended or adjusted under 35 U.S.C. 154(b) by 831 days.

(21) Appl. No.: 11/833,522

(22) Filed: Aug. 3, 2007

(65) Prior Publication Data

US 2008/0029447 A1 Feb. 7, 2008

Related U.S. Application Data

(60) Provisional application No. 60/821,683, filed on Aug. 7, 2006.

(51) Int. Cl.
*C12M 1/00* (2006.01)
*C12M 3/00* (2006.01)

(52) U.S. Cl. ............ 435/289.1; 435/291.1; 435/161; 435/162; 435/163; 202/83; 52/79.1; 52/79.7

(58) Field of Classification Search ........... 435/289.1, 435/291.1, 161, 162, 163; 202/83; 52/79.1, 52/79.7

See application file for complete search history.

(56) References Cited

U.S. PATENT DOCUMENTS

| 4,039,130 | A | * | 8/1977 | Hogan | 248/676 |
|---|---|---|---|---|---|
| 4,425,433 | A | * | 1/1984 | Neves | 435/163 |
| 5,545,543 | A | * | 8/1996 | Zinnamosca et al. | 435/162 |
| 5,656,491 | A | * | 8/1997 | Cassani et al. | 435/283.1 |
| 2003/0175182 | A1 | * | 9/2003 | Teall et al. | 422/188 |
| 2005/0260554 | A1 | * | 11/2005 | Gaalswyk | 435/3 |

* cited by examiner

*Primary Examiner* — William H Beisner
*Assistant Examiner* — Danielle Henkel
(74) *Attorney, Agent, or Firm* — Sturm & Fix LLP

(57) ABSTRACT

The present invention provides a modular ethanol production plant constructed of a number of identically sized modules each having a supporting structure main framework to which the components contained in the modules are attached. The plurality of modules includes a fermentation module, a distillation module, a ground grain module, and an optional heating module. Each of the modules are sized to occupy the same approximate space as a standard sized ocean going shipping container. Also, each of the modules has a central walkway including piping and electrical control boxes that are aligned for each connection to the next adjacent module.

11 Claims, 2 Drawing Sheets

SELF-CONTAINED DEPLOYABLE AUTOMATIC FACTORY BUILT ETHANOL PRODUCTION PLANT

CROSS REFERENCE TO RELATED APPLICATIONS

This application claims the benefit of U.S. Provisional Patent Application Ser. No. 60/821,683 filed Aug. 7, 2006 and entitled "Self-Contained Deployable Automatic Factory Built Ethanol Production Plant", which is incorporated herein by reference.

BACKGROUND OF THE INVENTION

1. Field of the Invention

The present invention relates to the field of chemical processing equipment, and more particularly to a modular production plant.

2. Description of Related Art

The high cost of energy coupled with improvements in genetic engineering has greatly improved the economics of making ethanol from grains. The current problem is that virtually all ethanol plants are currently built from scratch on site with large amounts of labor required for fabrication, plumbing, wiring and construction which greatly drives up the cost of construction and slows down the rate at which this ethanol producing technology can be put to widespread use.

As a consequence of the foregoing situation, there has existed a longstanding need for a new and improved modular ethanol production plant, and the provision of such a construction is a stated objective of the present invention.

BRIEF SUMMARY OF THE INVENTION

Briefly stated, the present invention provides a modular ethanol production plant constructed of a number of identically sized modules each having a supporting structure main framework to which the components contained in the modules are attached. The plurality of modules includes a fermentation module, a distillation module, a ground grain module, and an optional heating module. Each of the modules are the approximate size of a standard sized ocean going shipping container. Also, each of the modules has a central walkway including piping and electrical control boxes that are aligned for each connection to the next adjacent module.

BRIEF DESCRIPTION OF THE SEVERAL VIEWS OF THE DRAWINGS

These and other attributes of the invention will become more clear upon a thorough study of the following description of the best mode for carrying out the invention, particularly when reviewed in conjunction with the drawings, wherein.

DETAILED DESCRIPTION OF THE INVENTION

Figure 1:
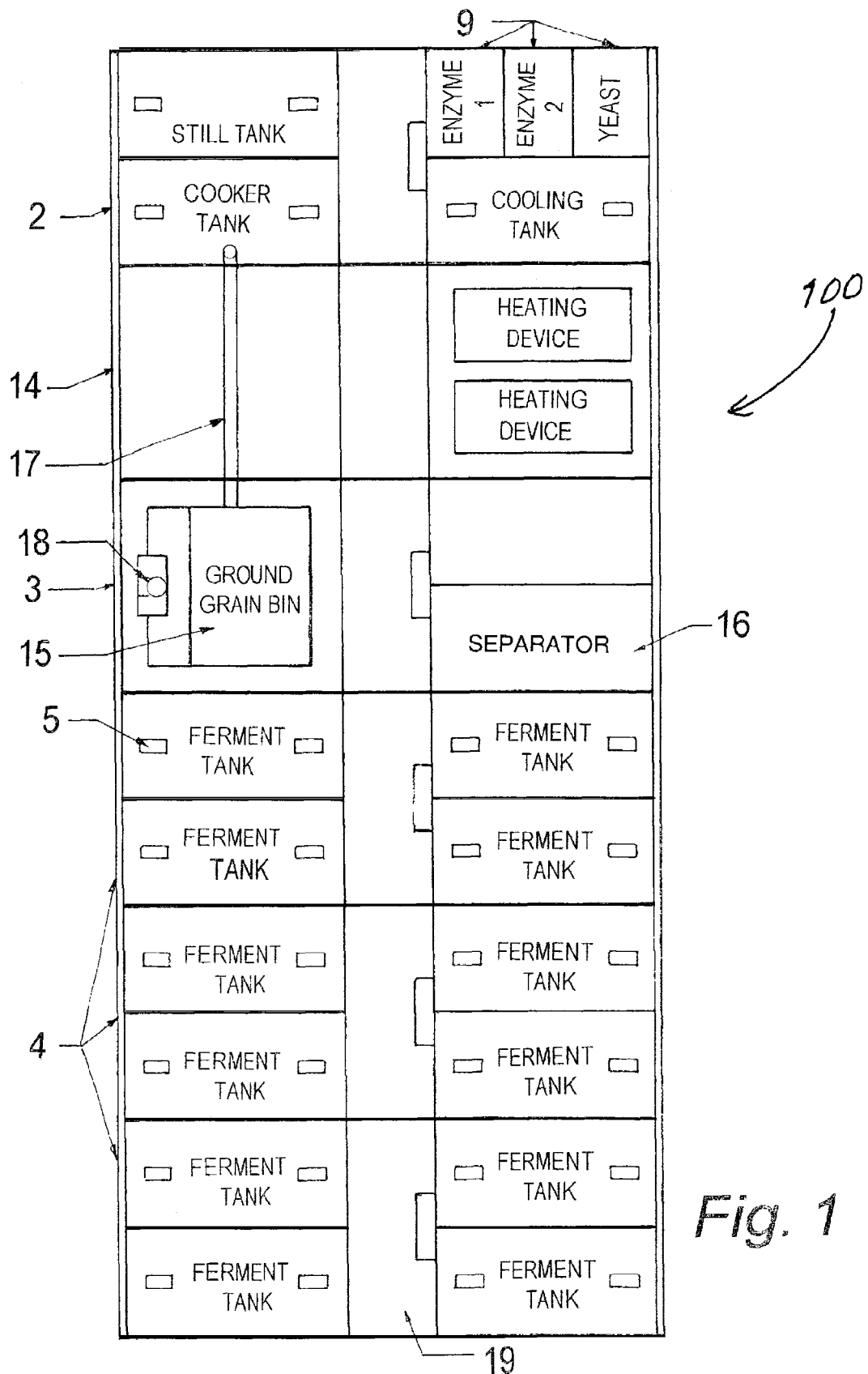
FIG. 1 is a top plan schematic view illustrating a number of interconnected, identically sized modules, that include the components needed for the production of ethanol from grain.
Figure 2:
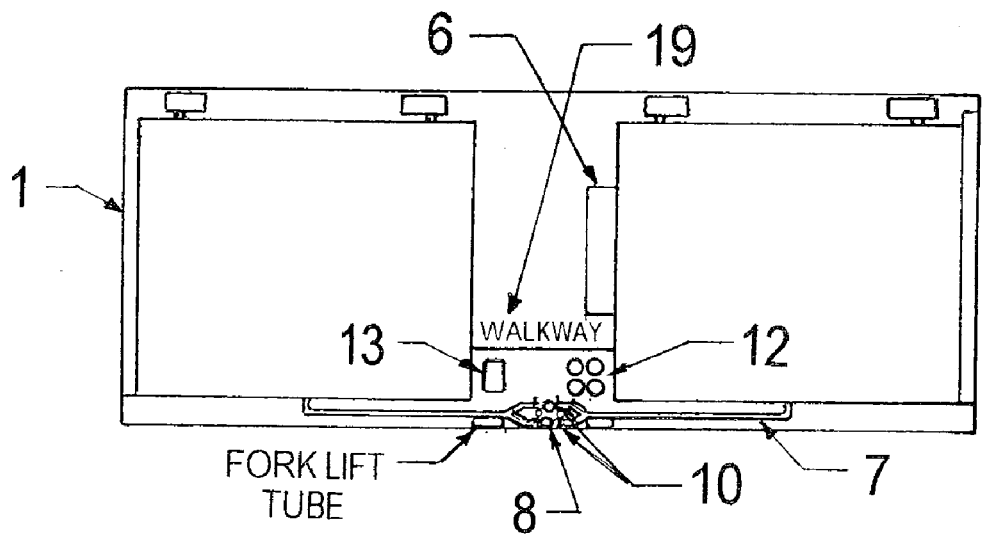
FIG. 2 is an end elevational schematic view of the fermentation module.
Figure 3:
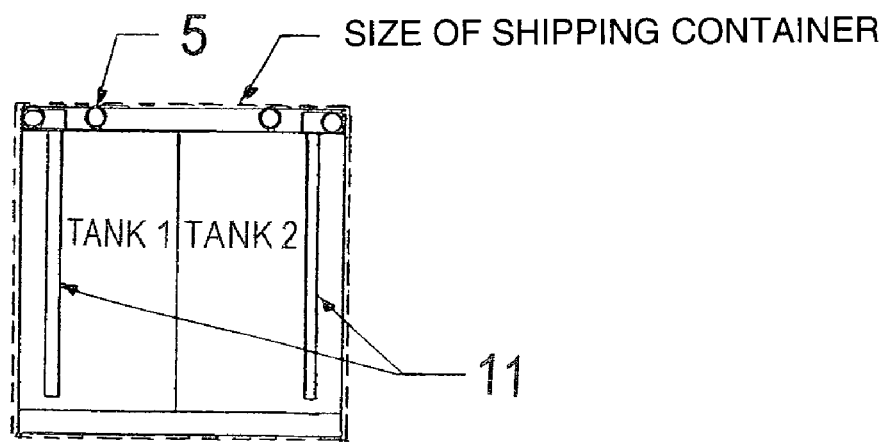
FIG. 3 is a side elevational schematic view of the fermentation module.

As can be seen by reference to the drawings, and in particular to FIGS. 1-3, the modular production plant that forms the basis of the present invention is designated generally by the reference number 100. This modular plant 100 is a self contained and portable automatic ethanol production plant that is manufactured ahead of time in a factory and delivered pre-wired and pre-plumbed to a side, ready to turn on and automatically produce ethanol with minimal on site installation labor required.

The system is built in pre-built modules 1 with each module 1 containing a supporting structure main framework consisting of longitudinal frame members which are rigidly connected by transverse members and vertical members to create a complete supporting framework to support equipment, piping, tanks, and electrical control equipment pre-plumbed and pre-wired at the factory where the units are built.

The overall design of the supporting structure is designed to be of the same approximate size and shape of a small or large ocean going shipping container. This allows the unit to be placed inside of a shipping container and shipped anywhere in the world. Shipping containers are typically eight feet wide and eight feet high by 20 or 40 feet long. The size utilized in the practice of this invention was designed to allow the placing of two of these modules in one eight foot by eight foot by 40 foot shipping container. Another practice of this invention may have made the units larger with only one module per shipping container. The smaller size was selected in this example to allow for smaller size fork lifts to be able to lift each module.

One of the pre-built modules contains tanks that are used for the fermentation process of making ethanol. Although the exact number is not a requirement of this patent, the fermentation module 4 utilized in this invention contains four separate tanks with three such modules 4 providing the twelve fermentation tanks often utilized together for a continuous producing ethanol production plant. The rectangular tanks were chosen because this would allow larger capacity tanks in the given space. Another practice of this invention would also be to use round tanks. Round tanks would clean out better, but the total tank capacity per module would be less.

Another of the pre-built modules 2 contain tanks that are used for the cooking, cooling and distillation process of making ethanol. A typical module configuration will contain one of these modules 2 with this module including one still tank, one cooking tank, one cooling tank, and optional yeast and enzyme tanks 9. These yeast and enzyme containers may be a tank or a hopper depending on if the material is liquid or dry. As yeast and enzymes continually improve, the necessity of including a separate cooking tank may not be needed within this module. Likewise, some practicing this invention may eliminate the cooling tank contained within the module and perform the cooling function directly within the fermentation tanks.

Each tank of each module has its own set of agitation devices located in the tanks with connected motors 5 located outside of the tank, but within the confines of the module. These motors 5 are connected and pre-wired at the factory to a control box 6, also mounted on the module that contain motor contactors and a programmable logic device or other computer process control system. Each of these tanks is plumbed using piping assembly 7 to a common flow piping 8 also mounted on the module.

Pneumatic controlled valves 10 (although valves of electric or other means of actuating could also be used to practice this invention), are pre-plumbed in the factory into each of the in-flow and out-flow pipe line assemblies. These valves are connected via control wires to the control panel 6 also located on the module.

Located on the cooking, cooling, and distillation module 2 are containers 9 utilized to store yeast, and the various enzymes used in the production of ethanol. These containers are also pre-plumbed at the factory to route and meter in the correct quantity of yeast or enzymes to the correct tanks when required by the master control system.

Routed within each of the tanks of either of the modules are heat exchanger coils 11 that are used for the cooling or warming of material to keep the material contained within the tank at the temperature as required for that segment of the ethanol production process. These heating or cooling coils 11 are routed and pre-plumbed at the factory to a common cold flowing liquid (water was used in this invention) piping assembly 12. Valves are pre-plumbed into these cold flow plumbing lines at the factory and the control wires are pre-wired back to the main control panel 6 located on the unit.

Routed within each of the cooking and distillation tanks are heat exchanger coils 11 of piping through which a warm liquid material will be pumped as needed to warm up the contents of the tank to the desired temperature as required by the cooking or distillation process. (Although practiced in the example of this invention, modern yeast and enzymes can reduce or eliminate the cooking phase and thus allow the invention to be practiced without a cooking tank.) These warming coils 11 are pre-plumbed to a common warm flow source pipe with control valves that are connected back to the control panel 6 mounted on the unit.

A separate optional module 14 contains the equipment necessary to warm the material that is to be routed to the warming heat exchanger coils located in each of the tanks. The equipment utilized to warm the material may be a natural gas burner, corn burner, electric heating coils, or microwave device. The actual equipment contained within this optional module may be different for each site as the costs of energy will vary per site. This source of hot flowing material may also be provided by an external source, such as a boiler.

Each of the modules will contain at least one pump 13 that is used to pump material out of the tanks contained within the module to the next desired location for that material. These pumps are pre-wired at the factory back to the main control panel 6 and already plumbed into the correct plumbing assembly 8.

A grinding and separating module 3 contains an optional hammer mill 18 that grinds the raw grain and conveys the ground grain up into a ground grain bin 15. This ground grain bin 15 is supported by a weighing device that is connected to the process controller located within the control box 6. The hammer mill 18 is optional as some practicing this invention may decide to grind the grain externally and simply convey the ground material into the ground grin weight hopper directly. The ground weigh hopper is utilized so that the process controller can weigh the exact amount needed for each batch of ethanol processed. When the computer process control determines that ground grain needs to be added to the cooker tank, an auger 17 conveys the grain into the cooker tank.

The grinding and separating module 3 also contains the equipment 16 required for separating the material left over in the fluid resulting once distillation is completed. The equipment contained within this module separates the solid material from the liquid and dispenses the resulting solid material to an externally provided conveying device. Alternatively, the combined liquid/solid by product material may be fed directly to animals as animal feed in a liquid state with this last separation module not necessarily utilized.

The example of the invention shown includes a common walkway 19 that is created by each of the modules set side by side. Below the walkway 19 is all of the common piping and pumps. The design in this configuration allows for common piping 8 and 12 to be easily connected together. As each module is set in place, the piping from the adjoining module aligns exactly and a simple plumbing connection can connect all of the modules together. Likewise, the electrical connects between the modules can easily be connected by simply connecting the electrical control boxes 6 on each unit together.

Each of the modules can be easily delivered to a site by truck, placed next to each other on a flat surface and quickly connected together to make for a complete functioning ethanol plant. The units are connected both by means of coupling the pipes between the modules and also by connecting electrically the control boxes. This coupling together then makes for all of the modules all functioning together as a complete automatic system with common fluid piping and process control automation controls all working together in unison. For the embodiment of this invention, the complete final system consists of modules including one cooker/still/cooling module 2, three fermentation modules 4 making a total of twelve fermentation tanks, one ground grin/separation module 3 and an optional heat generation module 15. The final result is a complete functioning ethanol production plant that was built in a factory, yet easily shipped and placed into operation anywhere in the world.

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

Having thereby described the subject matter of the present invention, it should be apparent that many substitutions, modifications, and variations of the invention are possible in light of the above teachings. It is therefore to be understood that the invention as taught and described herein is only to be limited to the extent of the breadth and scope of the appended claims.

I claim:

1. A modular ethanol production plant for producing ethanol from grain, comprising:
   a plurality of identically sized modules all operably interconnected together, the plurality of modules each including a supporting structure main framework having interconnected longitudinal frame members, transverse frame members, vertical frame members, and lateral sides;
   the plurality of modules including:
   a fermentation module having a fermentation tank, and fermentation tank pump operably connected to the fermentation tank;
   a distillation module having a still tank and a still tank pump operably connected to the still tank;
   a ground grain module having a ground grain bin and an auger operably connected to the ground grain bin;
   all of the plurality of modules being aligned such that at least one lateral side of each of the plurality of modules is connected to at least one lateral side of a next adjacent of the plurality of modules;
   each of the plurality of modules having common flow piping transversely disposed such that the common flow piping is aligned in all of the plurality of aligned modules, and the common flow piping is connected such that all of the plurality of aligned modules are in fluid communication with each other; and
   each of the plurality of modules having an electrical control box disposed such that the electrical control boxes are aligned in the plurality of aligned modules, and all of the control boxes are selectively connected such that all of the aligned modules are in electrical communication with each other, wherein, each of the plurality of modules includes a central walkway, wherein each central walkway is aligned with a next adjacent central walkway, and wherein the common flow piping is disposed below each central walkway, wherein the common flow piping is aligned below each adjacent central walkway, and the common flow piping is connected with a simple plumbing connection.

2. The modular plant of claim 1, wherein each of the plurality of modules is sized to fit within a standard sized ocean going shipping container.

3. The modular plant of claim 2 wherein the shipping container is approximately eight feet wide by eight feet high by twenty or forty feet long.

4. The modular plant of claim 1, wherein the fermentation module includes a plurality of fermentation tanks.

5. The modular plant of claim 1 wherein the distillation module further includes a cooking tank, a cooling tank, an enzyme container and a yeast container.

6. The modular plant of claim 1 wherein the ground grain module further includes a hammer mill operably connected to the ground grain bin.

7. The modular plant of claim 1 wherein the ground grain module further includes a solids-liquid separator.

8. The modular plant of claim 1 wherein the plurality of modules further include a heating module having a heating device operably connected to the fermentation module, the distillation module, and the ground grain module.

9. The modular plant of claim 1 wherein electrical control boxes are disposed within the central walkway, and the control boxes are disposed to be electrically connected to the control boxes in the next adjacent central walkway.

10. The modular plant of claim 1 wherein each of the plurality of modules includes a common cold flowing liquid piping assembly transversely disposed such that the common cold flowing liquid piping assembly is aligned in all of the plurality of aligned modules, and the common cold flowing liquid piping assembly is connected such that all of the plurality of aligned modules are in fluid communication with each other.

11. The modular plant of claim 10 wherein the common cold flowing liquid piping assembly is disposed below each central walkway, wherein the common cold flowing liquid piping assembly is aligned below each adjacent central walkway, and connected with a simple plumbing connector.

\* \* \* \* \*